United States Patent [19]
Nishimoto et al.

[11] Patent Number: 6,165,964
[45] Date of Patent: Dec. 26, 2000

[54] AQUEOUS SOLUTION OF ESSENTIAL OIL, AND ANTIMICROBIAL AGENTS, MICROBICIDES AND ANTIMICROBIAL FINISHES FOR WASHING

[75] Inventors: Tetsuro Nishimoto; Kiyohiro Nishimoto, both of Hiroshima, Japan

[73] Assignee: Cosmo Ace Co., Hiroshima, Japan

[21] Appl. No.: 09/254,641

[22] PCT Filed: Sep. 12, 1997

[86] PCT No.: PCT/JP97/03248

§ 371 Date: Nov. 29, 1999

§ 102(e) Date: Nov. 29, 1999

[87] PCT Pub. No.: WO98/11184

PCT Pub. Date: Mar. 19, 1998

[30] Foreign Application Priority Data

Sep. 13, 1996 [JP] Japan .................................. 8-243424

[51] Int. Cl.[7] .................................................. C11D 3/20
[52] U.S. Cl. .......................... 510/383; 510/102; 424/405
[58] Field of Search ..................... 510/102, 383; 424/405

[56] References Cited

U.S. PATENT DOCUMENTS 5,658,584  8/1997  Yamaguchi .............................. 425/405

FOREIGN PATENT DOCUMENTS

| | | |
|---|---|---|
| 51-135878 | 11/1976 | Japan . |
| 64-40402 | 2/1989 | Japan . |
| 5-271064 | 10/1993 | Japan . |
| 5-345899 | 12/1993 | Japan . |
| 6-263631 | 9/1994 | Japan . |
| 6-298619 | 10/1994 | Japan . |
| 7-97600 | 4/1995 | Japan . |
| 7-124197 | 5/1995 | Japan . |
| 7-133214 | 5/1995 | Japan . |
| 8-49172 | 2/1996 | Japan . |

*Primary Examiner*—John Hardee
*Attorney, Agent, or Firm*—Nixon & Vanderhye

[57] ABSTRACT

A process for the preparation of an aqueous hinokitiol solution, characterized by mixing hinokitiol or hinokitiol containing oil with water, boiling the obtained liquid mixture by heating, rapidly cooling the resulting liquid mixture, blowing oxygen into the liquid mixture under stirring, and storing the obtained liquid mixture at a temperature of 0.5 to 5° C. The process can give an aqueous solution of the water-insoluble essential oil having a concentration of up to about 40%. This aqueous solution of the oil is easily handleable by virtue of its liquidness, and does not contain any organic solvent harmful to the human body, thus being highly safe. Further, the solution has antibacterial and/or microbicidal effect.

3 Claims, 5 Drawing Sheets

AQUEOUS SOLUTION OF ESSENTIAL OIL, AND ANTIMICROBIAL AGENTS, MICROBICIDES AND ANTIMICROBIAL FINISHES FOR WASHING

TECHNICAL FIELD OF THE INVENTION

The present invention relates to an aqueous solution of essential oil and a process for preparing thereof. The present invention also relates to antimicrobial agents, microbicides and antimicrobial finishes for washing which contain the aqueous solution as an active ingredient.

BACKGROUND OF THE INVENTION

Various aromatic compounds are contained in woods and grasses, and various kinds of essential oil may be obtained from their leaves; blossoms, flowers, and their buds; barks, branches, stems and roots. Among these plants which contain such essential oil, there are crude drugs such as an aromatic stomachic, which have been used from ancient age. The essential oil, which is also the active ingredient for the crude drug, is a liquid mixture of several ten to two hundred compounds such as terpenoides, polyterpenoides, and phenols, and the rate of terpene is major.

As mentioned above, the essential oil may be obtained from various plants, but several essential oils obtained from trees such as *Juniperus virginiana* L., *Cypress sempervirens* L. var. *stricta* Ait., *Chamaecyparis obtusa* (Seib. et Zucc.) Endl. forma *formosana* Hayata, *Juniperus utilis* Koidz., *Chamaecyparis obtusa* Endl., *Chamaecyparis formosensis* Matsum., *Thujopsis dolabrata* Seib. et Zucc. var. Hondai Makino have anti-microbial activities or microbicide activities. Among such essential oils, it is known that hinokitiol contained in those obtained from *Chamaecyparis obtusa* (Seib. et Zucc.) Endl. forma *formosana* Hayata or *Thujopsis dolabrata* Seib. et Zucc. var. Hondai Makino has antimicrobial activities.

Hinokitiol is an acidic crystalline having a seven membered ring, and it is contained in the leaves or trees of *Chamaecyparis obtusa* (Seib. et Zucc.) Endl. forma *formosana* Hayata in Taiwan or the leaves, branches and stems of *Thujopsis dolabrata* Seib. et Zucc. var. Hondai Makino grown up in Aomori prefecture or Hokkaido.

Compounds detected as the components contained in the essential oils have a low molecular weight, and many of them are oily and a few of them are hydrophilic. Accordingly, it is difficult to mix the essential oil and water without using any surface active agent.

In general, oil and water can not be mixed homogeneously, but they may be mixed homogeneously depending on their mixing ratio. For example, a homogenous aqueous liquid can be prepared by extracting essential constituents with hot water from particular sources, soup for Chinese noodle or broth from a dried bonito is thus obtained. In such extract, a small amount of oil is dissolved in water. In the industrial process, for example, oil is vaporized by using contrabo to expose it to oxygen or other gas materials under pressure and at a certain temperature to allow the oil to mix with water.

However, the above-mentioned process includes the following problems. In the extracting process, the production cost is expensive, and it is impossible to produce such extract in a large scale. In the process by using contrabo, such extract may be produced in a large scale, but the cost is expensive. Furthermore, this process is performed under enhanced pressure and high temperature, the chemical structure of the objective components can be changed, and this makes it difficult to obtain an the aqueous extract containing the objective components.

Accordingly, such extracts can be used only for goods having high added value, for example, foods, food additives, and pharmaceuticals. Furthermore, in some cases, it is impossible to use aqueous extracts containing objective compounds with unchanged chemical structure.

It is known that hinokitiol is a compound having a seven-membered ring structure, and having excellent antimicrobial activity, particularly, antifungal activity, as well as it is safe compounds because resistant strains to hinokitiol scarcely appear. Therefore, wooden material from *Chamaecyparis obtusa* (Seib. et Zucc) Endl. forma *formosana* Hayata) has been used for a counter in sushi restaurant. Further, it is known that antimicrobial agents for washing having hinokitiol incorporated therein view of its antimicrobial properties.

On the other hand, hinokitiol has lower antimicrobial activities and no rapid action, as compared to antibiotics with high antibacterial activities and exhibiting rapid action. Accordingly, hinokitiol has been employed in the fields of dermatology, dentistry, and cosmetics.

Recently, however, an antibiotic resistant strain is increasing, particularly, methicillin-resistant multi-drug resistant Staphylococcus aureus, which is referred to as MRSA, appeared and causes troubles such as nosocomial infection. Recently, Kobori et al. have studied about antibacterial activity of hinokitiol to MRSA, and they reported that the appearing ratio of resistant strain to hinokitiol is low (Katsuji Kobori, et al., Medicinal Assay, vol.42, No.10, suppl. 1639(19)–1642(22)). Therefore, hinokitiol gathers attention.

However, as described above, since hinokitiol is one of the component contained in certain kinds of essential oil, which is insoluble in water, and impossible to mix homogeneously with water without any surface active agent, etc. On the other hand, when a surface active agent is used to mix them, the chemical structure of hinokitiol is changed and the antibacterial activity of hinokitiol is decreased. Therefore, since the antibacterial agent for washing could not be produced in liquid form, powdery one has been produced, but powdery one has poor handleable. Furthermore, the essential oils extracted from naturally occurring materials are highly safe for human bodies, in constant to those synthesized artificially, but their high production cost limits the application thereof.

Accordingly, there is a need to produce a homogenous aqueous solution that contains hinokitiol but does not contain any surface active agent with low cost.

SUMMARY OF THE INVENTION

An object of the present invention is to provide a process for preparing an aqueous solution containing essential oil derived from a plant which comprises the steps of preparing a liquid mixture by mixing at least one kind of essential oil with water, heating the liquid mixture to boil and then rapidly cooling, dissolving oxygen in the liquid mixture by stirring, and then storing the liquid mixture at a temperature 0.5 to 5° C.

In the process, it is preferable to repeat at least twice the above-mentioned steps of dissolving oxygen in the liquid mixture and then storing the mixed liquid. Furthermore, it is preferable to continue the step of dissolving oxygen in the liquid mixture until the content of dissolved oxygen reaches at least 9 ppm at a temperature of 20° C. under an atmospheric pressure. It is preferable that the above-mentioned plant essential oil is selected from the group consisting of Formosan Hinoki oil, Lavender oil, Hiba oil, Lemon Balm oil and Gingko oil.

Another object of the present invention is to provide a process for producing an aqueous solution containing plant essential oil comprising the steps of preparing a liquid mixture by mixing water with not larger than 40% (v/v of water), based on the water of at least one kind of essential oil with stirring, dissolving oxygen in the liquid mixture by blowing a gas containing at least about 20% of oxygen therein, mixing the liquid mixture with water by spraying the liquid mixture from at least two nozzles, allowing to stand the liquid mixture obtained in the mixing step, and diluting the liquid mixture to prepare an aqueous solution containing the essential oil at a desired concentration.

It is preferable that the plant essential oil is selected from the group consisting of Formosan Hinoki oil, Lavender oil, Hiba oil, Lemon Balm oil, and Gingko oil.

A further object of the present invention is to provide an aqueous solution consisting of water and at least one kind of essential oil derived from a plant. In the present invention, it is preferable that the plant essential oil is selected from the group consisting of Formosan Hinoki oil, Lavender oil, Hiba oil, lemon Balm oil, and Gingko oil.

Still another object of the present invention is to provide an aqueous solution containing an essential oil derived from a plants, which is prepared by a process comprising the steps of mixing at least one kind of essential oil with water, heating to boil and rapidly cooling the mixed liquid, dissolving oxygen in the liquid mixture by stirring it, and then storing the liquid mixture at a temperature of 0.5 to 5° C. In the present invention, it is preferable that the plant essential oil is selected from the group consisting of Formosan Hinoki oil, Lavender oil, Hiba oil, Lemon Balm oil and Gingko oil.

Still another object of the present invention is to provide an aqueous solution containing an essential oil derived from a plant. It is preferable that the aqueous solution comprises an essential oil selected from the group consisting of the above-recited essential oils. It is preferable that the aqueous solution contains at least certain amount of an active component of the essential oil having an antimicrobial effect.

Still another object of the present invention is to provide a microbicide and/or a disinfectant comprising the plant an aqueous solution containing essential oil. The antimicrobial agent and/or microbicide have an antibacterial effect to multi-drug resistant *Staphylococcus aureus*, enteropathogenic *Escherichia coli* O-157, *Salmonella typhymrium*, and Legionella.

Still another object of the present invention is to provide an antimicrobial finish for washing comprising the plant an aqueous solution containing essential oil.

BRIEF DESCRIPTION OF DRAWINGS

In FIG. 1, water and an essential oil are poured into a stirring vessel 2 at a certain ratio, and then the support 6 of the stirring rods 4 is moved up and down to mix the liquid mixture solution M in the vessel 2.

In FIG. 2, a solution consisting of water and an essential oil at a certain ratio is poured into a stirring vessel 12. Then the air or gas containing at least 20% of oxygen is blown into the liquid mixture as bubbles through a pipe of a bubble generator, which extends through the bottom of the vessel 12. The liquid mixture M in the vessel 12 is sucked through a pipe 62 extending through a sidewall of the vessel 12 by a pump 61, and is mixed together by using a circulator 16.

In FIG. 3, a liquid mixture M composed of an essential oil and water at a certain ratio is poured into a stirring vessel 22, where M is stirred by a device 24 which extends through the bottom of the vessel 22. Furthermore, the liquid mixture M is pumped up through a pipe 72 extending through the side wall of the stirring vessel, by using pump 71, and is mixed together in a liquid mixture pumping device 26.

In FIG. 4, a liquid mixture M' composed of an essential oil and water at a certain ratio is poured into a stirring vessel 32, where the liquid mixture M' is mixed together by moving a support 34 of stirring rods 33 up and down. Furthermore, gas supply means 36 and 38 supply gasses containing at least about 20% of oxygen in bubble form to increase the content of oxygen dissolved in the liquid mixture M'.

PREFERRED EMBODIMENT OF THE INVENTION

In the specification, the term "essential oil" means oily or semisolid substances from various plants or animals. In general, the essential oil is a composition comprising several dozens of compounds, and each essential oil component, i.e., each compound, contained in them, also referred to as "essential oil".

The essential oil employed in the present invention may be either obtained from natural sources as described above by steam distillation, extraction or either means, or compounds prepared by synthesis.

When the essential oil is obtained, leaves from natural sources, trunks, limbs, branches, stems, roots, fruits, barks, flowers and blossoms, and flower buds of various plants are used as essential oil sources. If the objective components are thermally stable and do not contain water-soluble components, steam distillation is preferably employed. When the essential oil is obtained from fruit peel such as orange or lemon, cold press is preferably employed. If the objective components in the essential oil sources are water soluble, or thermally unstable and their properties are liable to be changed by heat, extraction is preferably performed without using water at a temperature as low as possible.

Specifically, as examples of the essential oils used in the present invention, there can be mentioned Hinoki oil, Lavender oil, Hiba oil and other essential oils. Of these, Hinoki oil, Lavender oil, Hiba oil, Lemon Balm oil, and Gingko oil are preferable, because they have antimicrobial effect and microbicidal effect.

Hiba oil is obtained from steam distillation of trunks, limbs, branches and leaves of *Thujopsis dolabrata* Seib. et Zucc. var. Hondai Makino grown in Aomori prefecture or Hokkaido. Of these, Hiba oil from Aomori prefecture, which is referred to merely as Hiba oil herein below, is preferably used in the present invention, because its hinokitiol content is high.

Formosan Hinoki oil is obtained from steam distillation of trunks, limbs, branches, roots and leaves of *Chamaecyparis obtusa* (Seib et Zucc.) Endl. forma *formasana* Hayata grown in Taiwan, which is referred to as Taiwan Hinoki, is preferably used in the present invention, because its hinokitiol content is high.

Formosan Hinoki oil or Hiba oil is obtained by steam distilling root tips of Taiwan Hinoki or Aomori Hiba. Alternatively, Hinoki oil may be purchased form Gosho trading company (Taiwan) to use.

In the present invention, Lavender oil, which is obtained by steam distillation from flowers of *Lavendula officinalis* Chaix. cultivated in France, Italy, Hungary, England, North America, Australia, and Hokkaido, also is preferably used.

Furthermore, Lemon Balm oil obtained from *Melissa officinalis*, and Gingko oil obtained from leaves or fruits of Gingko trees may be preferably used. Green tea oil obtained from *Thea sinensis* L. is also preferably used, because it has antimicrobial effect and microbicidal effect.

In the present invention, not only the composition composed of the above-mentioned several dozens of compounds, but also a single component such as, for example, hinokitiol may be used. Such single component may be either derived from a natural substance by purification of essential oil containing hinokitiol, or may be an artificially synthesized compound. Hinokitiol may also be used as those, which are commercially available from Tokyo Chemical Industries.

When mineral rich water is used as water in the present invention, essential oil and water are advantageously mixed. As an example of such water, water naturally contains not less than 5 ppm of minerals such as $SiO_2$, $TiO_2$, $A_2O_3$, $Fe_2O_2$, $Fe_2O_3$, $FeO$, $MnO$, $MgO$, $CaO$, $Na_2O$, $K_2O$, $P_2O_5$ and so forth may be used, or water added with such minerals may be used. For example, Ohiro stone (obtained at Asahi village in Yamagata prefecture, and supplied from Ohiro Mining), or Bakuhan stone (obtained at Shirakawa-go in Gifu prefecture) is added into water to supplement minerals. Component composition of Ohiro stone and Bakuhan stone are shown in Table 1.

TABLE 1

Component compositions of Ohiro stone and Bakuhan stone

| Components | Content of each component (weight %) | |
|---|---|---|
| | Ohiro stone | Bakuhan stone |
| $SiO_2$ | 68.26 | 69.8 |
| $Al_2O_3$ | 14.80 | 14.0 |
| $Fe_2O_2$ | 2.84 | 1.3 |
| $Fe_2O_3$ | 2.89 | 2.0 |
| $FeO$ | 1.85 | 3.6 |
| $MnO$ | — | — |
| $MgO$ | 2.45 | 3.2 |
| $CaO$ | 0.94 | 0.3 |
| $Na_2O$ | 0.01 | 0.26 |
| $K_2O$ | 0.09 | 0.20 |
| $P_2O_5$ | 1.60 | 1.06 |

The minerals contained in these stones are dissolved in water, and mineral rich water may be obtained.

The essential oil and water are mixed according to the following predetermined steps, and an aqueous solution containing essential oil is obtained.

At first, the essential oil and water are mixed in a liquid mixture preparing step. In this step, the essential oil is mixed with water generally at a concentration range of 10 to 70% by weight, preferably 20 to 40% by weight. If desired, the minerals described above are added to water so as to be not less than 5 ppm.

Then, the liquid mixture of essential oil and water are heated to be boiled in the heating and rapidly cooling step. The time for boiling is generally about 5 minutes. After boiling, the liquid mixture is cooled rapidly by placing in a refrigerator, etc. In general, the liquid mixture is preferably cooled to 0.5 to 5° C. in about 3 hours after boiling, because the mixing of the essential oil and water is promoted.

The heated and rapidly cooled liquid mixture is stirred in an oxygen dissolving step to supply oxygen into the liquid mixture to enhance the content of dissolved oxygen. The stirring may be carried out by any method provided that an enough amount of oxygen is supplied into the liquid mixture.

Figure 1:
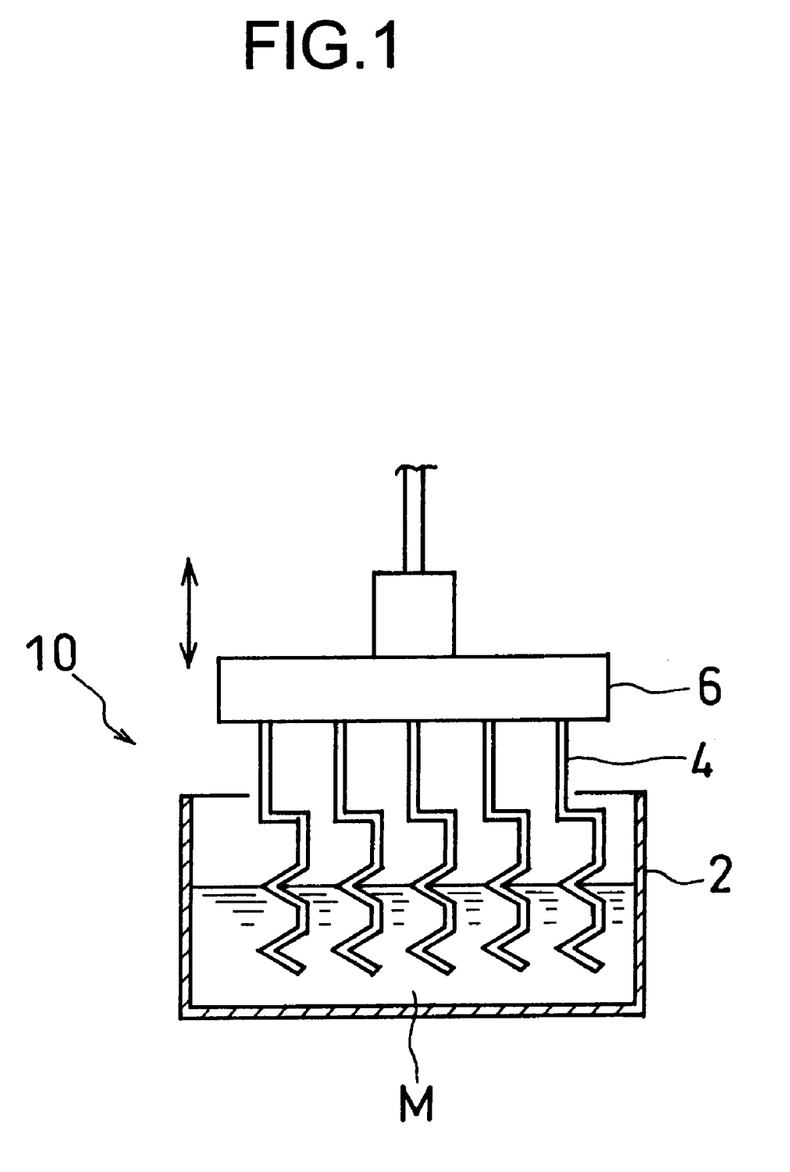
FIG. 1 is a schematic view illustrating one example of the equipment, used in the present invention, to mix water with an essential oil obtained from natural sources.

One example of the process for preparing the aqueous essential oil solution is shown in FIG. 1. The equipment 10 that may be used in the present invention comprises a vessel 2, a plurality of stirrer rods 4 and a support 6, which supports the stirrer rods 4, and the liquid mixture M is placed in the vessel 2. The stirrer rods 4 in this embodiment is composed of bar with zigzag form, but any type of stirrer rods may be used provided that it generates large resistance to the liquid mixture when it is moved up and down. For example, stirrer rods composed of bars that extend through a plurality of disks, or of spirally extending bars may be used as the stirrer rods 4.

In order to stir the liquid mixture M by using the equipment 10, the support 6 is moved up and down to give vertical motion to the stirrer rods 4. The vertical motion of the stirrer rods 4 supplies oxygen in the liquid mixture, and it may enhance the content of oxygen dissolved in the liquid mixture M. For enhancing the content of oxygen dissolved, it is preferable to give the vertical motion to the stirrer rods 4, rather than the rotational motion.

Figure 2:
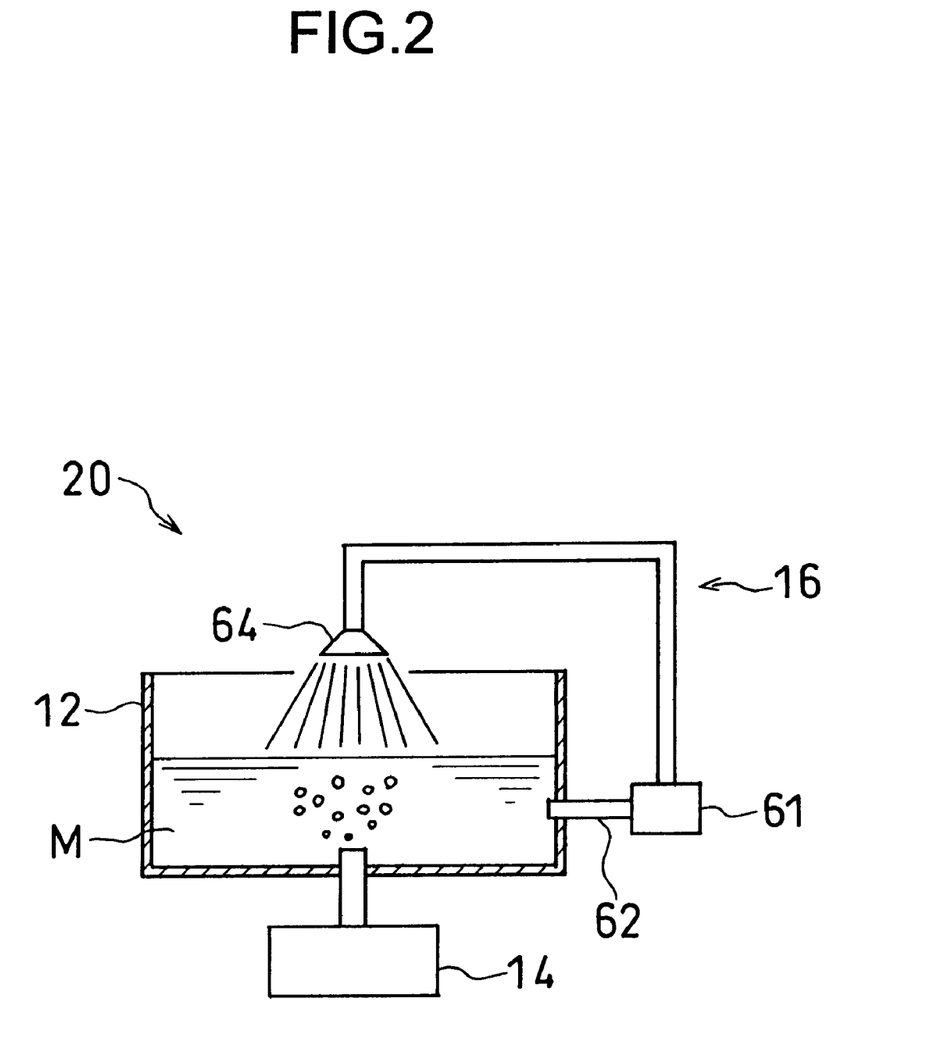
FIG. 2 is a schematic view illustrating one example of the equipment used for stirring in the process of the present invention.

Another example of the stirring method of the present invention is shown in FIG. 2. The equipment 20 that may be used in the present invention has a vessel 12 for a liquid mixture M, a bubble generator 14 of which tube extends through the bottom of the vessel 12 and a liquid mixture circulator 16. The bubble generator 14 has a function of generating and blowing the bubbles including air or oxygen into the liquid. The liquid mixture circulator 16 has the following structure: the liquid mixture M is sucked by a pump 61 through a pipe 62 which extends through the sidewall of the vessel 12, and sprayed through a nozzle 64 provided over the vessel 12.

For mixing the liquid mixture M by using the equipment 20, the liquid mixture M is sprayed from the nozzle 64, and the air or oxygen is blown from the bubble generator 14. The spraying of the liquid mixture M from the nozzle 64 is preferably performed under high pressure so as to jet the liquid mixture vigorously. Bubbling is preferably performed by a jet stream. When the oxygen is supplied by such method, the content of oxygen dissolved in the liquid mixture M is enhanced, but in some cases, either spraying the liquid mixture M or blowing the air or oxygen may be employed.

After the oxygen dissolving step, the resulting solution is generally stored at a temperature of 0.5 to 5° C. for 12 to 24 hours.

The procedures of stirring and storing described above are preferably performed at least twice. By repeating these procedures, the essential oil is easily dissolved into water because the content of dissolved oxygen is enhanced. Specifically, it is preferable to perform the procedures until the content of the dissolved oxygen reaches at least 9 ppm as measured under an atmospheric pressure at a temperature of 20° C. After the stirring and storing procedures, water is preferably added to the resulting essential oil-containing the aqueous solution and then the solution is filtrated. As filters, there can be mentioned, for example, those which are made of nylon or stainless steel with 20 to 50 mesh size and through which water is capable of passing.

According to the present invention, for example, an aqueous solution in which hinokitiol concentration is in the range of about 10 to 70% by weight is obtained, when Hinoki oil is used.

In the present invention, water and at least one kind of essential oil of which amount is not more than about 40% by weight, based on the water, are mixed together by stirring. When the essential oil to be added is not more than 20% by weight, based on the water, there is an effect that water and the essential oil may be mixed without the steps of boiling and cooling rapidly. Water to be mixed with the essential oil preferably contains minerals, and the mixing temperature is preferably in the temperature range of about 20 to 40° C., more preferably 25 to 30° C.

The essential oil may be mixed as a whole with water. However, in the liquid mixture preparing step, water and 10% by weight of the essential oil, based on the weight of water, are mixed and stirred; after mixing these two phases, additional 5% of essential oil is preferably added to the mixture and then repeated the same procedure. Finally, the aqueous solution containing essential oil in an amount of about 40% by weight, based on the water, is obtained.

Then, the liquid mixture is stirred by blowing the gas which contains at least about 20% (v/v) of oxygen to dissolve oxygen into the solution, because high content of oxygen dissolved in the mixture enhances the solubility of the essential oil. The gas to be blown is not particularly limited provided that it contains at least about 20% of oxygen, and there can be mentioned the air, oxygen gas, mixed gas of oxygen gas and inert gasses such as nitrogen gas, neon gas, and argon gas. In view of cost, the air is preferably used.

Figure 3:
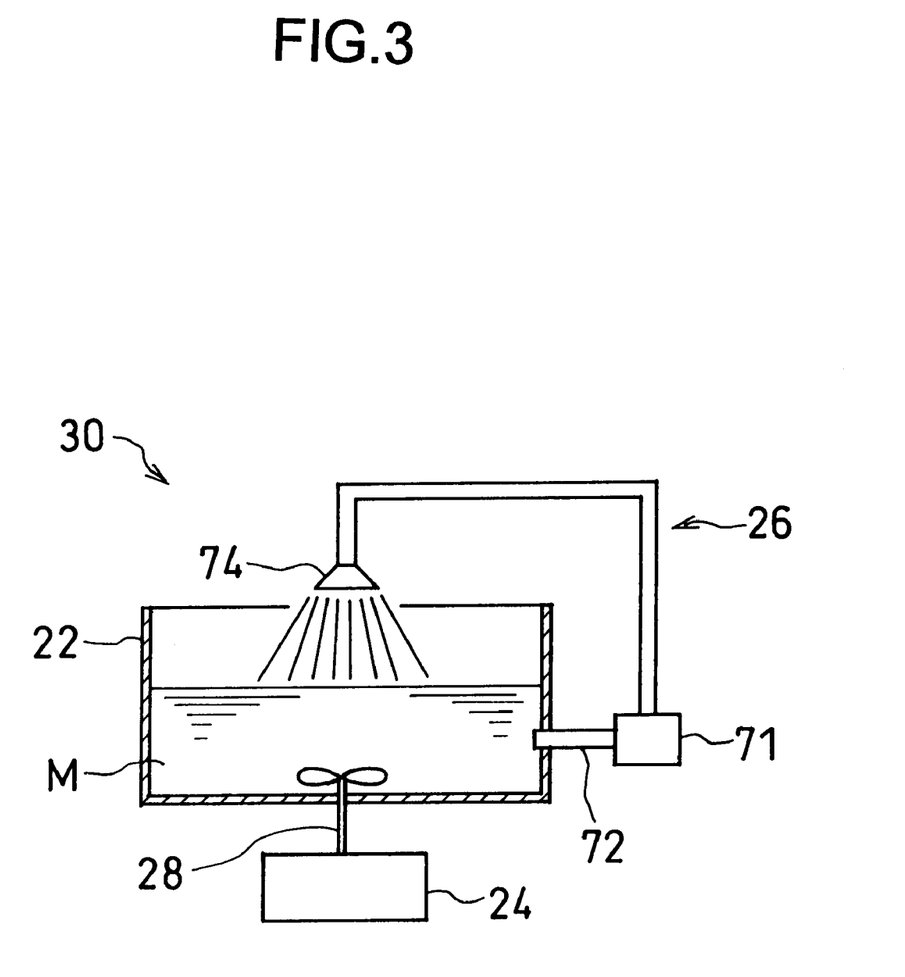
FIG. 3 is a schematic view illustrating another example of the equipment used for stirring in the process of the present invention.

FIG. 3 shows another example of the stirring method. An equipment 30 that may be employed in the present invention is composed of a mixing vessel 22 for the essential oil and water, a stirring device 24 having stirrer rods 28 extending through the bottom of the mixture vessel 22, and a mixture circulator 26. The stirring device 24 is used to mix water with the essential oil; and the stirring rods 28 is composed of a bar with or without impeller blades at the free end of it. The mixture circulator 26 may have a structure such that the liquid mixture M is sucked through a pipe 72 which extends through the sidewall of the mixture vessel 22 by a pump 71 to spray the mixture in a shower form from a nozzle 74 provided over the vessel 22.

In order to mix the liquid mixture M by using the equipment 30, the liquid mixture M is stirred with the stirring device 24, while spraying the liquid mixture M from the nozzle 74. Spraying of the liquid mixture M from the nozzle 74 is preferably performed with high pressure to vigorously eject the mixture.

Figure 4:
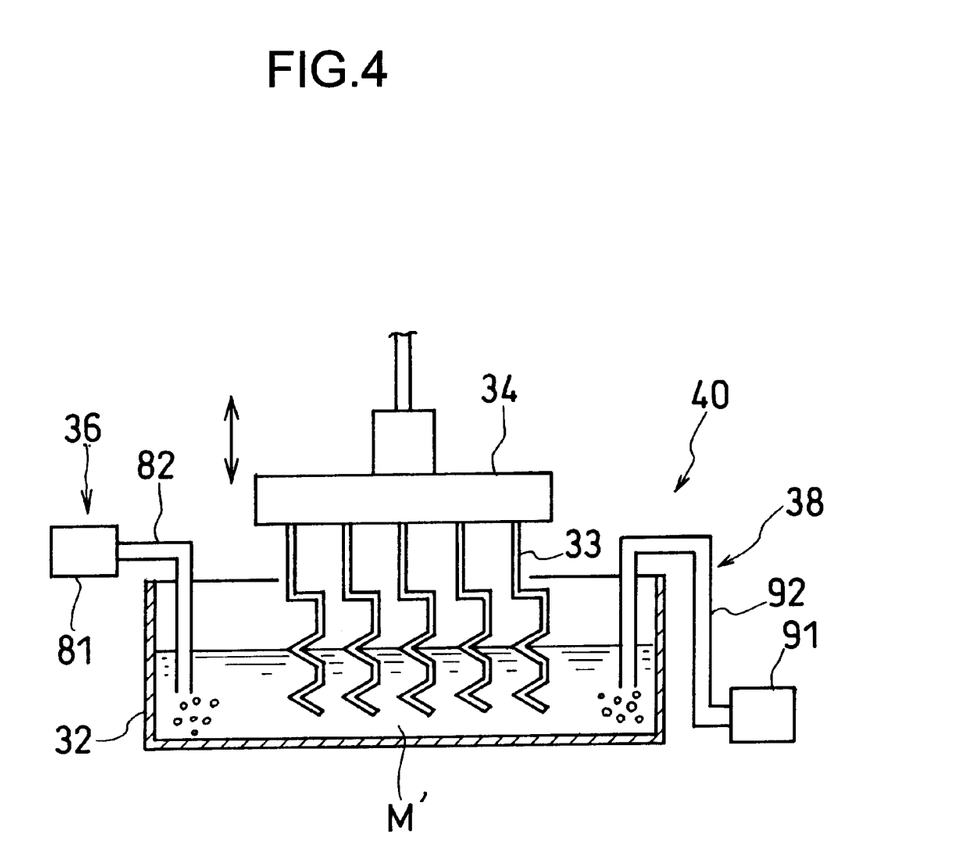
FIG. 4 is a schematic view illustrating another examples of the equipment used for stirring in the process of the present invention.

After completing this step, the resulting mixture is transferred to a device 40 shown in FIG. 4. The device 40 is composed of a vessel 32, gas supply means 36 and 38, a plurality of stirrer rods 33, and a support 34. The gas supply means 36 and 38 blow gas containing at least about 20% of oxygen into the liquid mixture M. When the number of the gas supply means used are varied depending on the size of the vessel so that water and the essential oil are mixed well. Briefly, if the vessel is small, the gas supply means may be used alone, and if the vessel is large, for example, four gas supply means may be used.

The resulting liquid mixture prepared in the mixing step is poured into the vessel 32. The support 34 is moved up and down to give a vertical motion to the stirrer rods 33, and the gas containing at least about 20% of oxygen is simultaneously supplied by a pump of the gas supply means. The stirring rods 33 are made of a bent hollow tube with zigzag shape. Suitable size of openings formed on the zigzag shape part of the stirring rods promotes mixing of the essential oil with water. The mixing is performed for a long time, for example, about 24 hours at a temperature of about 20° C., while blowing the gas into the mixture.

FIG. 4 shows that the stirrer rods 33 made of tubes with zigzag shape. As described above for the stirring rods 4 in FIG. 1, various shaped ones may be used instead of the stirrer rods with zigzag shape.

Figure 5:
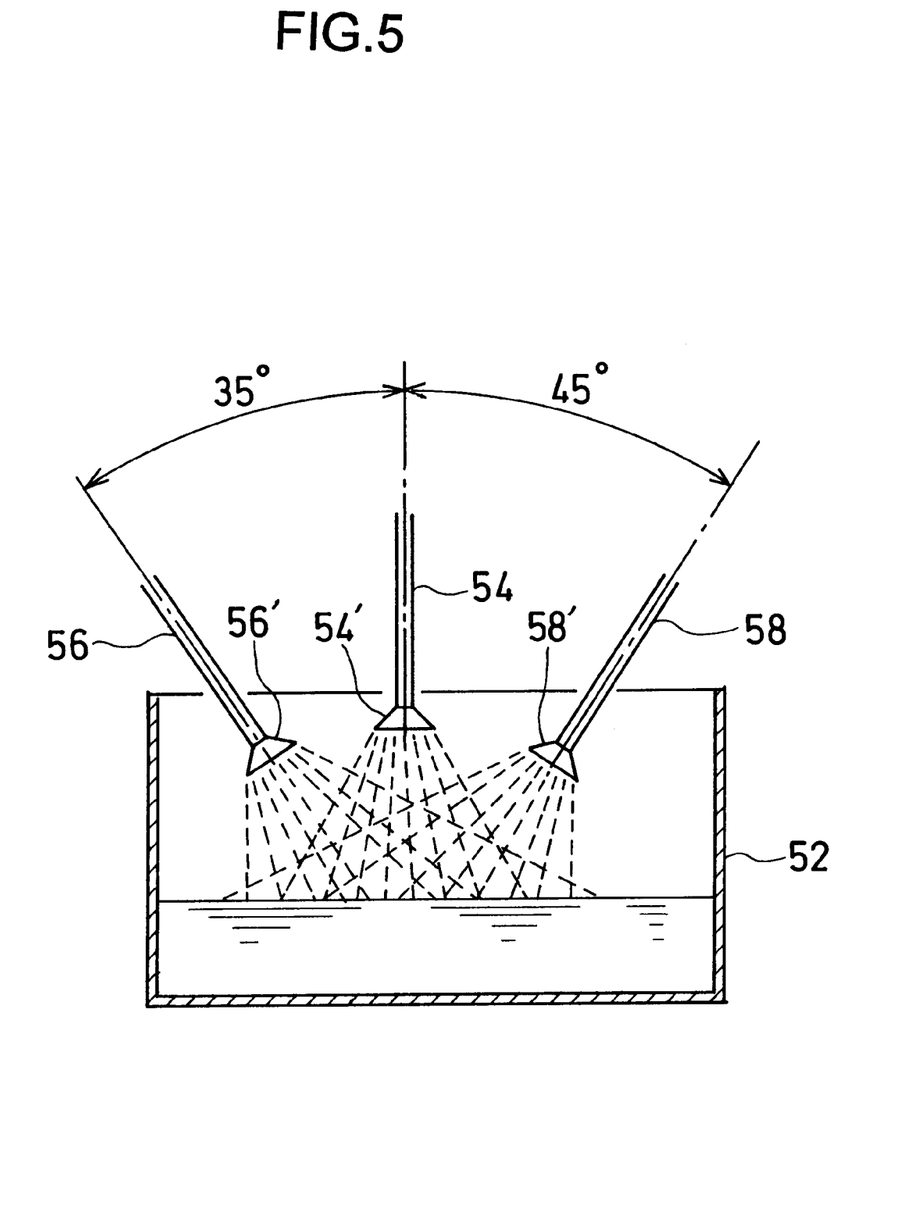
FIG. 5 is a schematic view illustrating another example of the device used for stirring in the process of the present invention. A pipe 54 having a nozzle 54' is vertical to the bottom of a vessel 52, and pipes 56 and 58 having nozzles 56' and 58' respectively are arranged at a predetermined angle to the pipe 54. The inner diameter of these pipes is the same.

Then, the liquid mixture prepared in the step of dissolving oxygen is fed to the step of mixing by pump. In the mixing step, the liquid mixtures fed through pipes 54, 56 and 58 are sprayed from nozzles 54', 56', and 58', which are arranged in a manner such that the liquid mixture sprayed there from impinge each other in the form of mist. More specifically, the pipe 54 with the nozzle 54' is arranged vertically to the bottom of a vessel 52; the pipe 54 with the nozzle 54' is arranged at an inclination angle of about 30° to 40° from the pipe 54 with the nozzle 54' and the pipe 58 with the nozzle 58' is arranged at an inclination angle of 40° to 50° from the pipe 54 with the nozzle 54'. It is preferable that the inclination angle between the pipes 54 and 56 is about 35°, and that between the pipes 54 and 58 is about 45°.

It is also preferable in view of the mixing efficiency and the production cost that the spraying from the nozzles are performed by using a compressor at a pressure of about 10 atm.

The temperature of the liquid mixture is preferably in the range of about 20° C. to 40° C., and more preferably in the range of about 25° C. to 35° C. The liquid mixture sprayed from each nozzle impinges upon another, and is collected in the vessel 52 as an aqueous solution containing essential oil.

The thus-obtained liquid mixture is allowed to stand for about 24 hours, and diluted with the above-mentioned water containing minerals to prepare an aqueous solution containing about 20% by weight of the essential oil. The aqueous solution containing essential oil may be further diluted with water to obtain an aqueous solution containing a smaller amount of the essential oil.

When the aqueous solution is used as antimicrobial agents and so forth, the solution is diluted to an extent such that an antimicrobial effect is manifested by the antimicrobial components in the solution. For example, when the Hiba oil and/or Taiwan Hinoki oil is used, the hinokitiol content is preferably in the range of at least 0.05% by weight but not larger than 0.5% by weight.

The antimicrobial agent or microbicide of the present invention comprises the above-mentioned aqueous solution of essential oil from plants. The antimicrobial agent or microbicide of the present invention is useful, because they exhibit broad antimicrobial spectrum to many kinds of microbials and do not generate resistant strain to them. For example, the antimicrobial agent and/or microbicide can be widely used for kitchen goods such as a kitchen towel, a cutting board, and knives; filters for an air conditioner, air cleaner and electric cleaner; and medical devices such as an inhalator, and a humidifier. Therefore, the antimicrobial agent or microbicide of the present invention is widely used in hospitals or food factories.

The treatment of articles with the antimicrobial agent and/or microbicide of the present invention are conducted by applying the antimicrobial agent and/or microbicide. For example, when aqueous solution containing Taiwan Hinoki oil or Hiba oil at a hinokitiol concentration of about 0.05 to 0.5% by weight is used, articles to be treated are immersed in the solution. The antimicrobial agent and/or microbicide of the present invention may also be used for washing hands. The antimicrobial agent and/or microbicide of the present invention show antibacterial spectrum for Staphylococcus, enteropathogenic *Escherichia coli*, Salmonella, and Legionella, in particular, it shows the antibacterial activities for MRSA or enteropathogenic *E.coli* O-157. Therefore, The antimicrobial agent and/or microbicide of the present invention are suitable as prophylactic or microbicide for serious infectious disease caused by such bacteria.

When the aqueous solution containing Taiwan Hinoki oil is used as the antimicrobial agent for hand washing, for example, an aqueous solution containing about 0.5% by weight of hinokitiol is preferred because it shows high antimicrobial and microbicidal activities.

Furthermore, since the aqueous solution containing essential oil from plant of the present invention is composed of volatile essential oil and water, and does not contain any surface active agent, it is highly safe. Therefore, even when a salient amount of the aqueous solution is spread out in a room, the solution hardly affects a human body in the room, and it does not remain bad smell in the room.

Since the antimicrobial finishes for washing of the present invention consisting of an aqueous solution containing essential oil from plant with is in a liquid form, it can be easily handled. For example, the finishes may be applied after washing of clothes with surface active agent and rinsing them, and before dehydration. Since the finishes of the present invention are liquid, it can be applied together with a softener or separately through a liquid-softener supply port. When the finishes are used, microbials on the clothes are disinfected and antibacterial activities are given. The finishes for washing of the present invention have merits such as deodorization, acaricide, and aromatization. Furthermore, since the essential oil in the finishes has excellent infiltration activity, it can degrade the components including the surface active agent or perfume molecule adhered on the clothes. Thus the finishes of the present invention have antimicrobial activities and acaricidal activities, and degrade the surface active agent; and thus it works as prophylactics for many diseases such as allergy, atopy, and asthma. The finishes for washing of the present invention hardly affect to the retraction and color fastness of the dyed clothes when they are applied.

When the aqueous solution containing Taiwan Hinoki oil is used as the antimicrobial finish, for example, about 10 ml of the solution that contains about 0.05% by weight of hinokitiol is added to 30 L of water.

According to the process of the present invention, the aqueous solution containing hinokitiol, which is insoluble in water, can be obtained. Since the hinokitiol containing-aqueous solution has liquid form, it is easy to handle and it contains no organic solvent harmful to human body. Also, the aqueous solution containing hinokitiol has antimicrobial activities, so that it is quite suitable for antibacterial agent or finish for washing.

The aqueous solution containing hinokitiol can be used to spray on filters of air conditioners or used as a suitable for filters instead of those in the air cleaners. The aqueous solution can also be used in a humidifier by adding it to water in it. When the aqueous solution containing hinokitiol is used in such application, it shows not only the antibacterial effect to inhibit growth of the various kinds of microbial in the air, but also it shows microbicidal effect. Accordingly, the aqueous solution prevents appearance of the clinical symptoms of atopy, allergy, or asthma patients caused by such microbe, and make the appeared clinical symptoms of them relax.

Furthermore, the aqueous solution can be sprayed directly onto face or body skin as skin lotion whereby *Staphylococcus aureus* on the skin can be deleted or the number of them can be decreased. Particularly, when the aqueous solution is used for a person who is immunosupressive, it effectively prevents infectious diseases via skin.

EXAMPLES

The present invention will now be explained by the following Examples in detail, that by no means limit the scope of the present invention.

Example 1

Process For Preparing Aqueous Solution-Containing Hinokitiol

Sixty parts by weight of water and 40 parts by weight of hinokitiol (purchased from Tokyo Chemical industries. Co.) were mixed. The obtained liquid mixture was heated and boiled for 5 minutes. After boiling, the liquid mixture was cooled down to a temperature range of 0.5 to 5° C. in about 3 hours in a refrigerator. Then, the liquid mixture was stirred by using the equipment 10 shown in FIG. 1. The chilled liquid mixture was poured in the vessel 2, and the up-and-down motion of the support 6 with the stirrer rods 4 was repeated for about 1 hour. After the stirring, the liquid mixture was stored at about 0.5 to 5° C. for about 24 hours. Then, the liquid mixture was stirred again for about 1 hour by using the equipment 10 shown in FIG. 1, and stored about 0.5 to 5° C. for about 24 hours. The content of oxygen dissolved in the stored liquid mixture was 9 ppm.

Then, the liquid mixture was filtrated by using a nylon filter with 300 mesh size. The filtrate was divided into three portions, and water was added to prepare three samples containing hinokitiol at the concentrations of 0.5% by weight, 0.05% by weight, and 0.005% by weight, and the samples were stored them at a temperature of 0.5 to 5° C. for three days.

Thus, aqueous solutions containing Hinokitiol at the above-mentioned concentrations were obtained.

Example 2

Process For Preparing Taiwan Hinoki Oil-Containing Aqueous Solution—1

An aqueous solution containing 0.5% by weight of Hinoki oil was obtained by the same process as described in Example 1, except that 40 parts by weight of Taiwan Hinoki oil (purchased from Goshou Trading Co.) was used instead of hinokitiol (purchased from Tokyo Chemical industries. Co.) in Example 1.

Example 3

Process For Preparing Taiwan Hinoki Oil-Containing Aqueous Solution—2

Water containing minerals was poured into the vessel 22 in the equipment 30 shown in FIG. 3, and essential oil having hinokitiol was added at a ratio of 10% by volume based on that of water. Water and the essential oil in the mixing vessel was pumped up by the pump 71 and ejected through the nozzle 74, while being stirred by the stirring device 24. The liquid mixture returned into milky white by conducting the pumping, and then 5% by volume of the essential oil having hinokitiol based on that of water was added, and the pumping was repeated. The essential oil containing hinokitiol was added again and the procedure of pumping-up was repeated, thus the liquid mixture containing 20% by weight of the essential oil was finally obtained.

Then, the liquid mixture was introduced into the vessel 32 in the equipment 40 shown in FIG. 4, and then stirred. The liquid mixture was stirred by moving up and down the support 34 with stirrer rods 33 for about 24 hours, while blowing the air supplied by the pumps 81 and 91 of the gas supply means into the mixed liquid.

After the mixing step was completed, the stirred liquid mixture was turned into mist by spraying out from three nozzles 54', 56' and 58' at a pressure of 10 atoms. The nozzles were arranged so as to fine droplets of the liquid mixture sprayed from each nozzle impinged one another. The arrangement of these three nozzles and the impingement of the fine droplets sprayed from them are shown in FIG. 5. The fine droplets from the nozzle 54' were fallen in vertical direction to the bottom of the vessel 52. The directions of the fine droplets from the nozzles 56' and 58' were inclined at 35° and 45°, respectively, to the direction of the droplets from the nozzle 54' at the centerline of their stream.

The impinging misty droplets formed larger droplets and were collected entrapped in the vessel 52. Thus, the resulting aqueous solution contained about 20% of Taiwan Hinoki oil.

Then a storage vessel was filled with the thus-obtained liquid mixture to prevent it from contacting with the air, and the liquid mixture was allowed to stand for about 24 hours at a temperature of about 20° C. After that, the liquid mixture was diluted with mineral containing water to 25 to 300 times, to obtain an aqueous solution containing Taiwan Hinoki oil.

pH of the aqueous solution was 6.7 by using glass electrode.

Examples 4

Preparation of Lavender Oil-Containing Aqueous Solution

About 3 kg of Lavender flowers were subjected to steam distillation to obtain about 300 g of Lavender oil. An aqueous solution containing Lavender oil was prepared in a manner similar to the process of Example 3 except that the Lavender oil obtained here was used instead of Hinoki oil.

Example 5

Antibacterial Effect of the Hinokitiol-Containing Aqueous Solution to *Staphylococcus aureus*-1

The three hinokitiol-containing aqueous solutions, containing 0.5% by weight, 0.05% by weight and 0.005% by weight of hinokitiol, prepared in Example 1, were used as test samples for the test of their antibacterial activities.

*Staphylococcus aureus* IFO 12732 was cultured on NA medium (Nutrient agar medium, purchased from Eiken Chemical Co.) for 16 to 24 hours at 35° C. After the cultivation, grown bacteria was suspended at about $1 \times 10^8$/mL of distilled water to use it as a bacteria solution.

The solutions A and B which contain 0.5% and 0.05% by weight of hinokitiol, respectively, were used as test samples as they were. The solution C which contains 0.005% by weight of hinokitiol was treated by heating at 60° C. for 20 minutes, and then used as a test sample. An ethanol solution that contains 49.5% of ethanol was used as a control sample.

Half mL of the bacteria solution was added to 50 mL of each sample. The mixture was maintained at 20° C. for 15 minutes, and then diluted by 10 times with SCDLP medium (supplied by Nihon Pharmaceutical Co.). The number of viable bacterial cells were determined in these diluted samples according to mixed dilution plate culture wherein the bacteria was cultured at 35° C. for 48 hours on SCPLPA medium, and then the number was expressed in terms of those per mL. The results are shown in Table 2.

Table 2 Microbicidal effect of the hinokitiol-containing aqueous solution to

TABLE 2

Microbicidal effect of the hinokitiol-containing aqueous solution to *Staphylococcus aureus*

| | Viable bacteria cell number (/mL) | |
|---|---|---|
| Samples | initial | 15 minutes after |
| Control | $2.8 \times 10^6$ | $1.5 \times 10^6$ |
| A | $2.8 \times 10^6$ | >10 |
| B | $2.8 \times 10^6$ | >10 |
| C | $2.8 \times 10^6$ | >10 |

Example 6

Microbicidal Effect of the Hinokitiol-Containing Aqueous Solution to MRSA-2

MRSA (*Staphylococcus aureus* ATCC 43300) was added to 9 mL of each of the hinokitiol-containing aqueous solutions A to C containing 0.5% by weight (A), 0.05% by weight (B) and 0.005% by weight (C), respectively, of hinokitiol, which were prepared in Example 1, in the range of $10^4$ to $10^5$ CFU/mL as the final concentration. These samples were allowed to stand for predetermined period, from 3 minutes to 3 hours at room temperature, and then the number of bacteria was counted. As the control sample, 9 mL of physiological saline was used.

Viable cell number in physiological saline was determined, and the number was used as the inactivation ratio of 0%. The inactivation ratio of each hinokitiol-containing aqueous solution to MRSA was calculated. The results are shown in Table 3.

TABLE 3

Bactericidal effect of the aqueous solution to MRSA

| Treatment time | | Viable bacteria cell number (/mL) | | |
|---|---|---|---|---|
| (min.) | control | A | B | C |
| 3 | $1.0 \times 10^5$ | $2.2 \times 10^3$ (97.80) | $8.4 \times 10^4$ (84.00) | $5.2 \times 10^4$ (52.00) |

TABLE 3-continued

Bactericidal effect of the aqueous solution to MRSA

| Treatment time | Viable bacteria cell number (/mL) | | | |
|---|---|---|---|---|
| (min.) | control | A | B | C |
| 30 | $8.9 \times 10^4$ | <10 (>99.99) | $1.6 \times 10^4$ (82.02) | $3.2 \times 10^4$ (96.40) |
| 60 | $3.0 \times 10^5$ | <10 (>99.99) | $4.3 \times 10^4$ (85.67) | $1.4 \times 10^3$ (99.53) |
| 180 | $2.4 \times 10^5$ | <10 (>99.99) | $4.0 \times 10^1$ (99.98) | <10 (>99.99) |

Accordingly, when any of the hinokitiol-containing aqueous solution is used to treat the samples, more than 80% of MRSA was inactivated in 30 minutes by the treatment, and more than 85% in 60 minutes by the treatment.

Example 7

Bactericidal Effect of the Hinokitiol-Containing Aqueous Solution to *Salmpnella typhimurium*

Aqueous solutions containing hinokitiol, containing 0.5% by weight (Solution A), 0.05% by weight (Solution B) and 0.005% by weight (Solution C), respectively, prepared in Example 1, were used as test samples. Bactericidal activities were tested as follows.

*Salmpnella typhimurium* IFO 12529 was cultured in bullion medium for disinfectant assay at 35° C. for 24 hours. Culture broth was centrifuged, and its precipitate was suspended in sterilized physiological saline at a concentration of about $1 \times 10^7$ cfu/mL. The suspension was used as Salmpnella solution.

Each aqueous solution of hinokitiol was diluted with sterilized distilled water by 500 times and used as the samples. 49.5% ethanol solution was used as a control sample.

Ten mL of each of the thus prepared sample was placed in a test tube with ground glass stopper. Then 1 mL of the Salmpnella solution is inoculated into the tube, and maintained at 20° C. for 1 minute. One platinum loop of Salmpnella solution is inoculated into the bullion medium for the disinfectant assay. Salmpnella in the bullion medium was cultured in the medium at 35° C. for 48 hours, and their bactericidal activities were evaluated based on whether the medium became turbid or not. In the entire samples and control sample, the growth of the Salmpnella was not observed.

Example 8

Microbicidal Effect of the Hinokitiol-Containing Aqueous Solution to *Escherichia coli* (*E.coli*)

Similarly to Example 5, microbicidal activities to *Escherichia coli* ATCC 25922 were evaluated. The results are shown in Table 4.

TABLE 4

Microbicidal activities of hinokitiol-containing aqueous solution to *E. coli*

| Treatment time | Viable bacteria cells (cfu/mL) | | | |
|---|---|---|---|---|
| (minutes) | Control | A | B | C |
| 3 | $1.7 \times 10^4$ | <10 (>99.99) | $1.3 \times 10^4$ (23.53) | $1.2 \times 10^3$ (29.41) |
| 30 | $1.5 \times 10^4$ | <10 (>99.99) | $4.0 \times 10^3$ (73.33) | <10 (>99.99) |
| 60 | $9.9 \times 10^4$ | <10 (>99.99) | <10 (>99.99) | <10 (>99.99) |
| 180 | $1.3 \times 10^4$ | <10 (>99.99) | <10 (>99.99) | <10 (>99.99) |

Any of the hinokitiol-containing aqueous solution inactivated more than 73% of *E.coli* by the treatment for 30 minutes.

Example 10

Microbicidal Effect of Hinokitiol-Containing Aqueous Solution Effect to Enteropathogenic *Escherichia coli*

Similarly to Example 5, microbicidal activities to enteropathogenic *E. coli* O-157 (*Escherichia coli* ATCC 35150) were evaluated. The results are shown in Table 5.

TABLE 5

Bactericidal activities of hinokitiol containing aqueous solution to *E. coli* O-157

| Treatment time | Viable bacteria cells (cfu/mL) | | | |
|---|---|---|---|---|
| (minutes) | Control | A | B | C |
| 3 | $1.2 \times 10^5$ | $3.0 \times 10^2$ (>99.99) | $8.4 \times 10^4$ (20.00) | $7.2 \times 10^4$ (40.00) |
| 30 | $1.5 \times 10^4$ | <10 (>99.99) | $2.6 \times 10^4$ (74.00) | $2.0 \times 10^4$ (80.00) |
| 60 | $1.2 \times 10^5$ | <10 (>99.99) | $7.5 \times 10^4$ (>37.50) | <10 (>99.99) |
| 180 | $1.5 \times 10^5$ | <10 (>99.99) | $3.5 \times 10^3$ (97.67) | $3.0 \times 10^1$ (99.98) |

Any of the hinokitiol-containing aqueous solution inactivated more than 70% of enteropathogenic *E.coli* O-157 by the treatment for 30 minutes.

Example 11

Microbicidal effect of the hinokitiol-containing aqueous solution to *Salmpnella typhimurium*

Each aqueous solution containing hinokitiol which respectively contains 0.5% by weight (Solution A), 0.05% by weight (Solution B) and 0.005% by weight (Solution C) prepared in Example 1 was used as test samples. Microbicidal activities were tested as follows.

*Salmpnella typhimurium* IFO 12529 was cultured in bullion medium for disinfectant assay at 35° C. for 24 hours. Culture broth was centrifuged, and the precipitate was suspended in sterilized physiological saline at the concentration of about $1 \times 10^7$ cfu/mL. The suspension was used as Salmpnella solution.

Each the aqueous solution containing hinokitiol was diluted with sterilized distilled water by 500 times to use as the sample. 49.5% ethanol solution was used as a control.

Ten mL of thus prepared samples was placed in a test tube with a glass stopper. Then 1 mL of the above-mentioned Salmpnella solution is inoculated into the tube, and maintained at 20° C. for 1 minute. One platinum loop of Salmpnella solution is inoculated into the bullion medium for the disinfectant assay. Salmonella in the bullion medium was cultured in the medium at 35° C. for 48 hours, and their microbicidal activities were evaluated based on whether the medium became turbid or not. In all of the samples and control, the growth of the Salmpnella was not observed.

Example 12

Microbicidal Effect of the Hinokitiol-Containing Aqueous Solution to Legionella pneumophila ATCC 33154

Similarly to Example 5, microbicidal activities to Legionella (ATCC 33154) were evaluated. The results are shown in Table 6.

TABLE 6

Microbicidal activities of the aqueous solution containing hinokitiol to Legionella (ATCC 33154)

| Treatment time | Viable bacteria cells (cfu/mL) | | | |
|---|---|---|---|---|
| (hour) | Control | A | B | C |
| 1 | $2.6 \times 10^5$ | $1.0 \times 10^2$ (99.96) | $8.2 \times 10^3$ (96.85) | <10 (>99.99) |
| 3 | $2.5 \times 10^5$ | <10 (>99.99) | <10 (>99.99) | <10 (>99.99) |

Any of the hinokitiol-containing aqueous solution inactivated more than 96% of Legionella (ATCC 33154) by the treatment for 1 hour.

Example 13

Antimicrobial Test of the Hinokitiol-Containing Aqueous Solution

Antimicrobial test was performed according to the procedure of determining bacteria number written in the processing effect evaluation manual (Ed. by Textile Goods Hygienic Processing Committee, 1988).

After socks were washed with a house held washing machine and then they were treated with an aqueous solution containing hinokitiol. Briefly, 10 mL of an aqueous solution containing 0.05% by weight of hinokitiol (B) was added into 30 L of water in the washing machine. As test sample pieces, parts of these socks (0.2 g) were used. As reference sample pieces, parts of other socks (0.2 g) that were not treated with hinokitiol containing solution were used. As non-treated standard sample pieces, parts of standard white cloth made of nylon (0.2 g) were used.

Staphylococcus aureus ATCC 6538P was suspended in sterilized liquid bullion to prepare a suspension, and 0.2 mL of the suspension, which contains about $4 \times 10^5$ cells of Staphylococcus aureus, were inoculated on each sample piece. Then, these sample pieces with bacteria were cultured at 37° C. for 18 hours. The number of viable cells on the sample pieces before and after culturing were counted, and the ratio and value of cell number increase or decrease, as well as the difference between the value of cell number increase or decrease were calculated according to the following equations.

The ratio of cell number increase or decrease *1
= (viable cell number on the test sample pieces after 18 hour culture)/(viable cell numbers immediate before culture (inoculated cell number))

The value of cell number increase or decrease *2
= $\log_{10}$[(viable cell number on the test sample pieces after 18 hour culture)/(viable cell number immediate before culture (inoculated cell number))]

The difference of the value of cell number increase or decrease *3
= (the value of cell number increase or decrease on non-treated sample)−(the value of cell number increase or decrease on treated sample)

The results are shown in Table 7.

TABLE 7

Antibacterial effect to Salmpnella washed with hinokitiol containing aqueous solution

| | Antibacterial effect | | |
|---|---|---|---|
| Samples | *1 | *2 | *3 |
| Detergent alone | $6.3 \times 10^2$ | 2.8 | 0.0 |
| Detergent + B | $1.6 \times 10^2$ | 2.2 | 0.6 |
| Non-treated standard sample | $6.3 \times 10^2$ | 2.8 | — |

When the sample pieces were washed with a surface active agent plus the hinokitiol-containing aqueous solution, the number of Salmpnella cells decreased to ¼ of those treated with the surface active agent only or the non-treated standard samples. Therefore, it is shown that the hinokitiol-containing aqueous solution has antimicrobial effect.

Example 14

Shrinkage Ratio Measurement Test For Clothes Treated With the Hinokitiol-Containing Aqueous Solution Socks, white and black underwear, black sleeveless shirts, navy blue tank top and briefs were washed according to the procedure 103 of JIS L-1042 G. Then, they were treated with the hinokitiol-containing aqueous solution (B) prepared in Example 1, and then were hang out for drying. The shrinkage in lengthwise direction and crosswise direction (%) were measured and their ratio was calculated. For comparison, textile goods, which were not treated with the aqueous solution containing hinokitiol, were dried by the same way, and the shrinkage ratios were calculated.

TABLE 8

Shrinkage test of clothes treated with the aqueous solution containing hinokitiol

| | | Treatment method | |
|---|---|---|---|
| Samples | | JIS103 | JIS + B |
| Socks | Straight-up ribbed top | | |
| | width | 1.4 | 4.3 |
| | length | 0 | 0 |
| | Total length | 6.0 | 9.2 |
| | Sole size | 8.0 | 9.2 |
| Underwear | lengthwise | 3.0/5.3 | 2.7/4.7 |
| (Black and White) | crosswise | −3.5/−2.0 | −4.0/−1.3 |

TABLE 8-continued

Shrinkage test of clothes treated with the aqueous solution containing hinokitiol

| Samples | | Treatment method | |
| --- | --- | --- | --- |
| | | JIS103 | JIS + B |
| Sleeveless shirts | lengthwise | 1.7 | 1.3 |
| | crosswise | 4.7 | 2.7 |
| Tank tops | lengthwise | 3.7 | 3.3 |
| | crosswise | 1.0 | 1.0 |
| Briefs | lengthwise | 7.5 | 2.5 |
| | crosswise | 1.5 | 7.5 |

As shown in Table 8, it was not observed that the clothes treated with the aqueous solution shrunk to significant degree.

Example 15

Color Fastness Test of the Clothes Treated With Hinokitiol-Containing Aqueous Solution Socks, white and black underwear, black sleeveless shirts, navy blue tank tops, and briefs were washed according to the procedure 103 of JIS L- 1042 G. Then, they were treated with the aqueous solution containing hinokitiol and hang out for drying. Discoloration and color fading of those clothes was evaluated by using gray scale discoloration, or color fading was observed. Accordingly, there was no problem for color fastness.

Example 16

Release Promotion Test of Surface Active Agent by the Hinokitiol-Containing Aqueous Solution Socks, white and black underwear, black sleeveless shirts, navy blue tank tops, and briefs were washed according to the procedure 103 of JIS L-1042 G. They were rinsed twice with tap water in reservoir. The tap water was prepared by adding 10 mL of an aqueous solution containing 0.05% by weight of 0.05% hinokitiol (B) into 30 L of water. The amounts of surface active agent released from the clothes in the first and second rinse solutions are shown in Table 9.

TABLE 9

Detergent release promotion test for the aqueous solution containing hinikitiol

| Treatment | Amounts of the detergent in the rinse solution (mL/L) | |
| --- | --- | --- |
| | 1st | 2nd |
| With B | 19.0 | 6.2 |
| Without B | 4.6 | 1.7 |

As shown in Table 9, the amounts of surface active agent in the rinsing solution with the aqueous solution containing hinokitiol was more than those in the rinse solution without the hinokitiol-containing aqueous solution. As the result, it is shown that the hinokitiol-containing aqueous solution promotes the removal of surface active agent from fibers.

Industrial Applicability

According to the process of the present invention, an aqueous solution containing essential oil from plant can be obtained by mixing water and essential oil, which is insoluble in water without any additives such as surface active agents.

The aqueous solution containing essential oil from plant has broad antimicrobial spectrum, and it is useful as the microbicides. Furthermore, it is available as antimicrobial finishes for washing.

In addition, since the aqueous solution of the present invention has high safety and microbicidal effect, it is useful as substitutes for filters of air cleaners, or for water for humidifiers. The solution may also be used as an additive to water in a reservoir.

What is claimed is:

1. An essential oil-containing aqueous solution consisting of 90 to 30% by weight of water and 10 to 70% by weight of essential oil selected from the group consisting of hinoki oil, hiba oil, lavender oil, lemon balm oil and ginko oil.

2. An antimicrobial agent consisting of 90 to 30% by weight of water and 10 to 70% by weight of essential oil selected from the group consisting of hinoki oil, hiba oil, lavender oil, lemon balm oil and ginko oil.

3. An antimicrobial agent as claimed in claim 2, wherein said antimicrobial agent has an antimicrobial effect against bacteria selected from the group consisting of Staphylococcus, enteropathogenic *Escherichia coli*, Salmonella and Legionella.

\* \* \* \* \*